United States Patent
Fishbaugh

[19]

[11] Patent Number: 5,970,515
[45] Date of Patent: Oct. 26, 1999

[54] PROTECTIVE EYEWEAR

[76] Inventor: Brenda B. Fishbaugh, 1410 Georgetowne Park Dr., Ft Wayne, Ind. 46815

[21] Appl. No.: 09/158,992

[22] Filed: Sep. 23, 1998

[51] Int. Cl.$^6$ .................................................. A61F 9/04
[52] U.S. Cl. .................................................. 2/15; 128/858
[58] Field of Search .................... 2/11, 15; 128/857, 128/858; D16/300, 301, 302, 305, 306, 307, 308

[56] References Cited

U.S. PATENT DOCUMENTS

| | | | |
|---|---|---|---|
| 2,165,668 | 7/1939 | Vaccaro | 2/15 |
| 2,341,673 | 2/1944 | Walker | 2/14 |
| 2,527,947 | 10/1950 | Loos | 128/163 |
| 2,572,638 | 10/1951 | Loos | 128/163 |
| 3,068,863 | 12/1962 | Bowman | 128/132 |
| 3,092,103 | 6/1963 | Mower | 128/132 |
| 3,269,267 | 8/1966 | Collins | 88/112 |
| 3,300,786 | 1/1967 | Rosenvold et al. | 2/2 |
| 3,619,815 | 11/1971 | Towner, Jr. | 2/12 |
| 3,756,692 | 9/1973 | Scott | 350/160 P |
| 3,780,379 | 12/1973 | Kampman | 2/15 |
| 4,024,405 | 5/1977 | Szot | 250/516 |
| 4,122,847 | 10/1978 | Craig | 128/132 |
| 4,162,542 | 7/1979 | Frank | 2/15 |
| 4,411,263 | 10/1983 | Cook | 128/132 R |
| 4,567,122 | 1/1986 | Baldry et al. | 430/4 |
| 4,701,962 | 10/1987 | Simon | 2/15 |
| 4,793,002 | 12/1988 | Simon | 2/12 |

OTHER PUBLICATIONS

"Silver Shades" product literature, Silver Shades International, Longboat Key, FL. (date unknown).

*Primary Examiner*—Diana Oleksa
*Attorney, Agent, or Firm*—Barnes & Thornburg

[57] ABSTRACT

A film segment with a novel shape for forming an eye protector and a method for using the film segment is described. The shaped film segment is used to form an improved eye protector with an increased field of vision and improved fit to the facial tissues adjacent the eye.

31 Claims, 2 Drawing Sheets

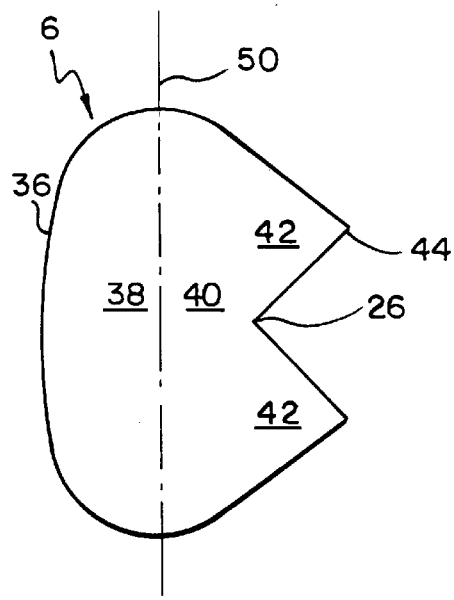
FIG. 8
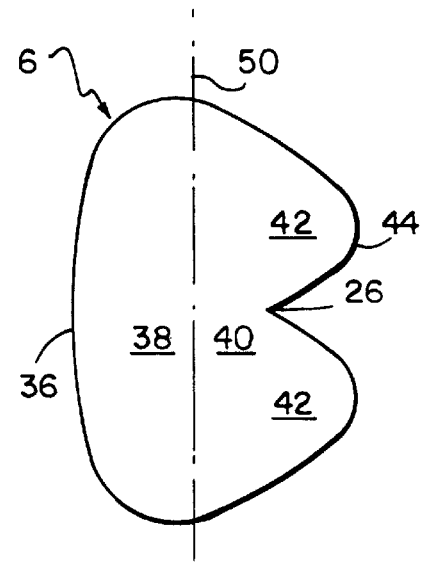
FIG. 9
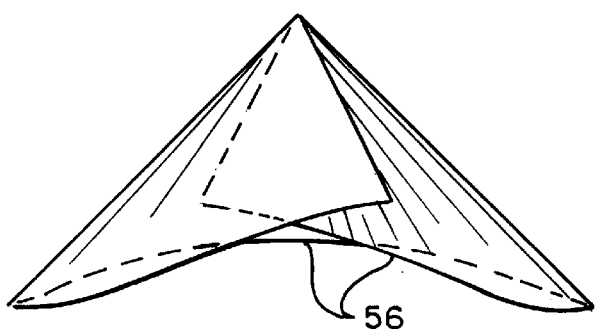
FIG. 12
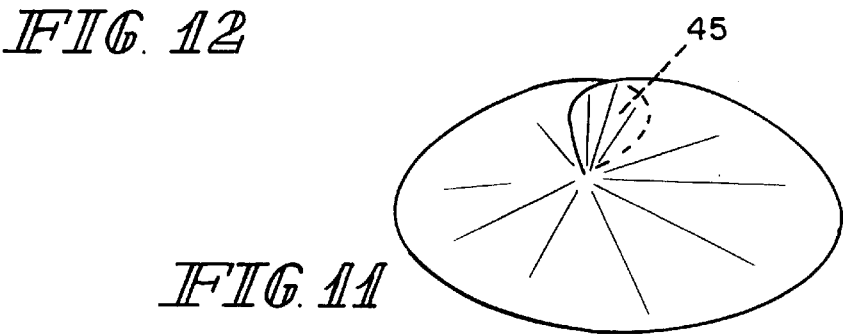
FIG. 10
FIG. 11

PROTECTIVE EYEWEAR

FIELD OF THE INVENTION

This invention relates to disposable protective eyewear. More particularly, the present invention is directed to adjustable eye protectors shaped for improved eye protection, user comfort, and visibility.

BACKGROUND AND SUMMARY OF THE INVENTION

Intense visible light or radiation of shorter wavelength, i.e., between about 200 and about 400 nanometers (ultraviolet radiation), from the sun or from artificial light sources poses a significant risk of eye injury. The eye is particularly susceptible to damage from exposure to ultraviolet radiation because the damaging radiation cannot be sensed by the light receptors in the eye. Thus, ultraviolet (UV) radiation is invisible to the eye, and the injury is not apparent until after the damage is done. While the UV radiation component of sunlight can damage the eyes without proper precaution, the majority of cases of UV radiation eye damage arise from the use, or more appropriately the misuse, of artificial sunlamp products in the home or in commercial tanning salons. Responsive to that fact, federal regulations have been promulgated to specify safety standards for the manufacture and use of UV emitting products. One of those regulations (21 C.F.R. § 1040.20) requires that protective eyewear be provided and used with all UV emitting lamps. To comply with these regulations some lamp manufacturers and many tanning salon proprietors have been supplying customers with reusable goggle-type protective eyewear, which although functional to protect the eyes, are uncomfortable and not size-adjustable to fit each prospective user. Moreover, reusable protective eyewear presents certain sanitary problems—it can serve as a means for spreading communicable eye diseases of both microbial and viral origin. This fact, coupled with the prevalent fear of contracting certain viral infections, prompts many users of UV light emitting products to refuse to use appropriate protective eyewear. Reusable goggles, although available to the customer, are often simply not used.

Clearly the availability of a disposable, adjustable, and inexpensive eye protector for use with UV emitting devices and for use in other circumstances requiring temporary protection of the eye from potential eye irritants, would meet important public health and safety needs. Not only would such a device promote the use of appropriate eye protection at home and in the increasingly popular tanning salons, but it would also help to minimize the spread of disease possibly associated with reusable protective eyewear.

Several early inventors faced with the need for easy-to-use eye protectors developed and patented ocular patch-type protective eyewear in both disposable and reusable forms. See, for example, the eye protectors or eye shields disclosed in U.S. Pat. Nos. 2,165,668; 2,283,752; 2,572,638; 3,068,863; and 2,527,947. While the patch-type eye protectors disclosed in those early patents function to protect the eyes from potential eye irritants and harmful radiation, none of them were designed (1) to selectively transmit at least a portion of visible light so that the user can "see" while wearing the protective eyewear; (2) to be shaped to conform to the facial tissue adjacent the eye; or (3) to allow for substantially unhindered eye lid movement when the eye protector is positioned over the eye.

More recently, U.S. Pat. Nos. 4,739,002 and 4,701,962 (hereinafter referred to as the "'002 and '962 patents," respectively) disclosed disposable eyewear in which a conical eye protector is formed by overlapping and adhering portions of ovoid or circular film segments. Those film segments are formed to contain ultraviolet absorbing compounds, yet they allow sufficient visible light to pass through to enable the user to "see" while wearing this protective eyewear. The patented eyewear represented a significant advance in the field of protective eyewear because they were disposable, they allowed for some vision in use and they covered only the eye and the facial tissues adjacent to the eye.

The present invention is based on applicants' discovery that the film segments used for forming protective eyewear similar to that described in U.S. Pat. No. 4,739,002 can be formed to a novel shape that provides significant improvement in eyewear functionality. Eyewear formed from film segments in accordance with this invention (1) fit better to the facial tissue adjacent to the eye; (2) have an increased field of vision; (3) provide more room to open and close the eye; (4) cover less of the brow area adjacent to the eye; and (5) are more resistant to unintended damage during user manipulation of the segment to form the eyewear.

The improved film segments of this invention are formed to have a novel shape in plan view including a C-shaped edge segment and a W-shaped edge segment cooperating to define a peripheral edge. The general shape hereinafter is referred to as the "CW shape" and the shaped film segment is hereinafter referred to as "CW-shaped film segment". In one embodiment the film segment comprises a polymeric film having a radiation transmittance value of less than 1 for at least a portion of incident ultraviolet, visible or infrared radiation. A contact adhesive is applied to a locus of the segment including at least a portion of the peripheral edge defined by the W-shaped edge segment. The film segment is formed into an asymmetric conical shape by overlapping the portions of the film segment defined by the W-shaped edge segment. The adhesive at the locus of the W-shaped edge segment holds the overlapped portions in place and thus works to hold the segment in the conical eyewear shape. The eye protector is then located over the eye in an adhesively retained position. In practice, a pair of protectors are used, each one positioned to cover each eye.

BRIEF DESCRIPTION OF THE DRAWINGS

FIG. 8 is a diagrammatic silhouette of one embodiment of the present CW-shaped film segment;

FIG. 9 is a diagrammatic silhouette of another embodiment of the present CW-shaped film segment;

FIG. 10 is a plan view of the eye proximal side of the embodiment of the CW-shaped film segment shown in FIG. 9;

FIG. 11 is a top perspective view of the asymmetric cone-shaped eye protector as formed from the embodiment of the CW-shaped film segment shown in FIG. 10; and FIG. 12 is a side view of an asymmetric cone-shaped eye protector in accordance with the invention.

DETAILED DESCRIPTION OF THE INVENTION

Figure 1:
FIG. 1 is a perspective view illustrating one of the present eye protectors in use.

With reference to FIG. 1 there is provided in accordance with this invention protective eyewear 2 of generally asymmetrical conical shape for fitting over the eye so that its base is in contact with the soft tissue surrounding the eye. The eyewear of this invention is formed from film segment 6 having a unique shape (the "CW-shape") as shown best in FIGS. 2, 3 and 8–10. With reference particularly to FIGS. 8 and 9, the CW-shape can be defined with reference to the artificial line 50 bisecting film segment 6 into two portions 38 and 40: a portion having peripheral edge 36 shaped like a "C" (hereinafter the "C-shaped portion" 38); and a portion having peripheral edge 44 is shaped like a "W" (hereinafter, the "W-shaped portion" 40). As shown in FIGS. 8 and 10, peripheral edge 44 of the W-shaped portion 40 can have angled line edge segments or peripheral edge 44 can have round edge segments as shown in FIGS. 9 and 10. In each of those embodiments the CW-shaped film segment 6 has a C-shaped portion 38 adjoined to a W-shaped portion 40 so that the peripheral edge 36 of the C-shaped portion 38 joins peripheral edge 44 of the W-shaped portion 40.

Figure 2:
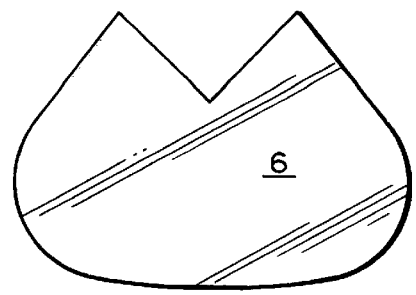
FIG. 2 is a plan view of a CW-shaped film segment used to form one of the present eye protectors.

With reference particularly to FIGS. 2, 10 and 11, a contact adhesive is applied to a loci 10 on one side of CW-shaped film segment 6. The locus 10 of applied adhesive is coincident with at least a portion of a peripheral edge 44. Preferably the locus 10 of the contact adhesive is coincident with a portion of both peripheral edges 36 and 44. Thus locus of contact adhesive coincident with a portion of peripheral edge 44, allows the lobes 42 of the W-shaped portion 40 of segment 6 to be adhesively connected when lobes 42 are manipulated along path 12 to an overlapping position with concomitant formation of eye protector 2.

The nature of the contact adhesive utilized in accordance with the present invention is not critical. Many synthetic acrylic and natural rubber-based contact adhesives are known in the art. Preferably, the contact adhesive is a non-allergenic, medical grade adhesive such as those which have been used on medical tapes and dressings. Such contact adhesives are commercially available, for example, in the form of a transfer tape with a release liner. Thus, in practice the shaped film segment 6 can be cut from a sheet of polymeric film or film laminate, hereinafter described, on which a transfer tape has been applied in a predetermined pattern so that the die cut film segments 6 each have the desired locus 10 of applied contact adhesive. In use, the adhesive is exposed on the film segment 6 by removal of the release liner; the film segment is formed into eye protector 2; and eye protector 2 is applied to cover the eye so that at least a portion of locus 10 of adhesive not in contact with underlapped lobe 45 (see FIG. 1) is in contact with flesh around the eye thereby functioning to adhesively secure eye protector 2 in position over the eye.

Figure 3:
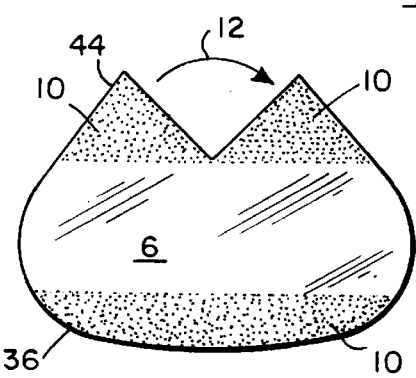
FIG. 3 is a plan view of a CW-shaped film segment with contact adhesive on the eye proximal side of the film segment.
Figure 4:
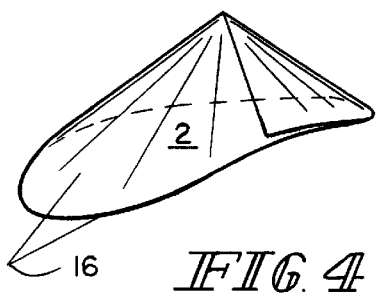
FIG. 4 is a perspective view of an asymmetric cone-shaped eye protector formed from the film segment shown in FIG. 3.
Figure 5:
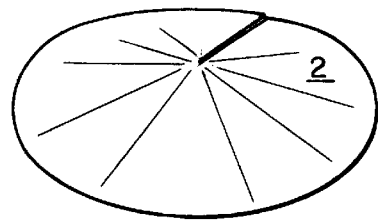
FIG. 5 is a top perspective view of an asymmetric cone-shaped eye protector formed from the film segment shown in FIG. 3.

With reference particularly to FIGS. 3 and 4, the CW-shaped film segment 6 having a locus 10 of applied adhesive is formed into an asymmetrical cone-shaped eye protector 2 so that the peripheral edge 36 of C-shaped portion 38 and at least a portion of peripheral edge 44 of W-shaped portion 44 of film segment 6 essentially forms the base 16 of the eye protector 2. FIGS. 5 and 11 illustrate asymmetrical cone-shaped eye protector 2 formed from the adhesive-bearing shaped film segments 6 illustrated in FIGS. 3 and 10, respectively.

Use of the unique CW-shaped film segment in accordance with this invention enables formation of eye protector 2 having improved user visibility and field of vision. Such improvement derives from the asymmetrical conical configuration of the eye protector formed from film segments 6 in preferred embodiments of the invention. Unlike the eye protectors illustrated in U.S. Pat. No. 4,701,962, the eye protector formed from CW-shaped film segment 6 has an asymmetrical conical shape wherein the apex 26 of eye protector 2 is located above and toward the perimeter of the base 16 (i.e., the apex is not located above the geometric center of the base). The eye protector described in the '962 Patent was conical. This distinction is important in that the apex and overlapped portions of the more symmetrical eye protectors in the art tend to create areas of high distortion 32 or no visibility at all near the "line of sight" center of the protector and obscure the wearer's view. The asymmetrical conical eye protector of this invention is formed and placed over the eye to minimize areas 32 with obstructed lines of sight. Use of the CW-shaped segment results in the apex of the eye protector being formed more proximate to the perimeter (in plan view) and tends to "open up" or broaden the field of vision by increasing the area 22 where visual distortion is minimal. The asymmetrical conical shape of the present eye protector results in a significantly less obstructed field of view than that provided by the eye protectors illustrated in the '962 patent.

Figure 6:
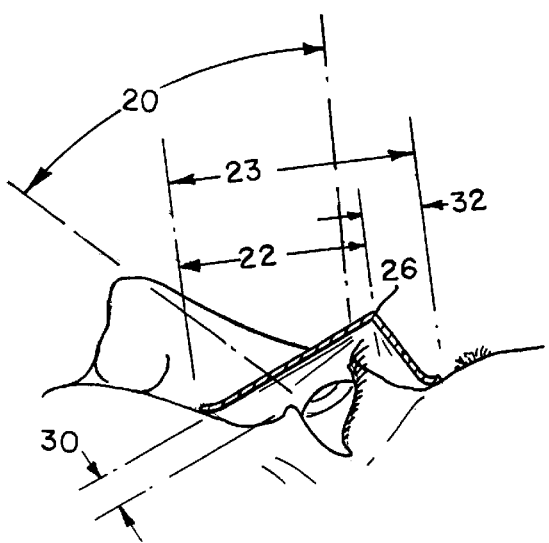
FIG. 6 is a cross-sectional side view of the asymmetric cone-shaped eye protector covering an eye.
Figure 7:
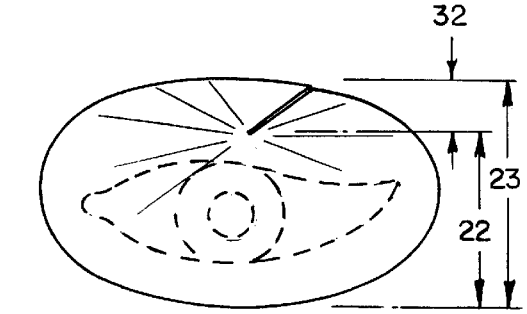
FIG. 7 is a top view of an asymmetric cone-shaped eye protector covering an eye.

FIGS. 6 and 7 show that when the eye protector is properly located over the eye (with overlapped portion toward the brow), the apex 26 is located so that it lies above the natural line of sight. Apex 26 and overlapped portions of the lobes 42 are located more to the periphery of the field of view 20.

In a preferred embodiment of the present invention, film segment 6 is formed into an asymmetric cone-shaped eye protector 2 by at least partially overlapping the lobes 42 of the W-shaped portion 40 to adhesively engage those overlapped lobes so that the peripheral edge portions 36 that are not overlapped essentially forms base 16 of asymmetric conical eye protector 2. The width 23 of eye protector 2, and to some extent the conformation of the base 16, can be adjusted by the amount of overlap of lobes 42. Thus, the size of base 16 of eye protector can be reduced, for example, by increasing the amount of overlap of the lobes 42.

Adhesively securing overlapped lobes 42 of CW-shaped film segment 6 forms asymmetric conical eye protector 2 in accordance with the present invention. With base 16 having arched portions 56 (see FIG. 12), which conform well to (above and below) the contours of the flesh immediately adjacent to the eye in the eye cavity. This advantageously allows for a good fit of the eye protector against the skin surrounding the eye when the eye protector is positioned to cover the eye.

As shown in FIGS. 6 and 7, the protective eyewear of the present invention covers only a small portion of the tissue lying between the eyelid and brow and fits snugly within the facial area defined by the eye orbital. This is important because one use of the present eye protectors is in tanning salons. The patrons of such salons prefer to maximize the facial tanning and thus facial exposure to UV radiation.

The composition of the film segment itself is not critical to the present invention so long as its spectral transmittance and other physical properties are such that it will afford the desired eye protection. For example, if in accordance with the present method, the eye protector is intended to protect the eye against eye irritants such as those which may be encountered in certain hair treatments, the film segment should be liquid impervious. The segment could be opaque, transparent or translucent. Since most users of protective eyewear prefer to "see" while the protective eyewear is in place covering the eyes, it is preferred in accordance with this invention to form the film segment from a polymeric film which is transparent to at least a portion of incident visible radiation.

In accordance with this invention, where the protective eyewear is used to reduce the exposure of an eye to ultraviolet radiation, the shaped film segment should be formed from a film comprising an ultraviolet light absorbing polymer. Ideally the film segment should be essentially opaque to ultraviolet light. Federal regulations specify that protective eyewear for use with UV emitting sunlamp products have a radiation transmittance of less than about 0.001 for radiation having a wavelength ranging from about 200 to about 320 nanometers and a transmittance value less than about 0.01 for radiation having a wavelength ranging from about 320 nanometers to about 360 nanometers.

Polymeric films suitable for use in accordance with the present invention are well known in the art and readily available commercially either as monolayer films or multi layer film laminates. Thus, the CW-shaped film segment 6 in accordance with the present invention can be formed from a monolayer or multi layer laminate of a polymeric film selected from acrylic polymers, for example, acrylate, methacrylate and copolymers thereof; polyethylene and copolymers of ethylene and other olefin monomers such as hexene-1 and butene-1; polypropylene; polyvinylchloride and copolymers thereof; nylon; and polyesters, for example, polyethylene terephthalate. Such polymeric films are well known in the art and are commercially available in thicknesses ranging from less than 0.5 mils to more than 10 mils (1 mil equals 0.001 inch).

The optical properties, and other physical properties, of an eye protector in accordance with the present invention are determined by the thickness and composition of the polymeric materials used for forming the CW-shaped film segment 6. For example, light transmittance of the film segment, and therefore that of the eye protector to be formed from that segment, can be produced by utilizing a vacuum metallized polymeric film, usually a biaxially oriented polymeric film, to form the CW-shaped film segment 6. In a preferred embodiment of this invention the CW-shaped film segment 6 is formed from a laminate of two or more polymeric films, at least one of which is a metallized biaxially oriented polyethylene terephthalate. Such metallized film laminates are well known in the art and have found utility as solar control film and as packaging material for various foods. The second polymeric film layer in such art-recognized laminates is typically a polyester or a polyolefin such as polyethylene. In another preferred embodiment of this invention, the CW-shaped film segment 6 is formed from a laminate of two or more polymeric films, at least one of which is a clear laminate layer of the CW-shaped film segment 6 and having at least one laminate layer incorporating a UV-absorbing material.

In a preferred embodiment of the present invention the eye protector is formed from a film segment having reduced transmittance of ultraviolet (UV) radiation. Some polymers, for example those containing aromatic ring structures and other UV absorbing functional groups, strongly absorb UV radiation and inherently have low UV transmittance. Other types of polymeric films not inherently having such UV absorbing polymeric groups can be modified by including art-recognized UV absorbing "stabilizers" during the polymer film formation process.

Commonly used UV absorbing or stabilizing compounds are substituted benzophenone and substituted benzotriazole compounds. The most common benzophenone compounds used as UV stabilizers for polymeric films are 2,4-dihydroxy-benzophenone, 2-hydroxy-4-acryloxyethoxybenzophenone, 2-hydroxy-4-methoxy-benzophenone, 2,2'-dihydroxy-4-methoxy-benzophenone, 2,2'-dihydroxy-4,4'dimethoxy-benzophenone, 2-hydroxy-4-n-octoxybenzophenone, 2,2',4,4'-tetrahydroxy-benzophenone, and 4-dodecyloxy-2-hydroxy-benzophenone. Most common of the substituted benzotriazoles used as UV stabilizers in polymeric films are 2(2'-hydroxy-5'-methylphenyl)benzotriazole, 2-(3,3',5'-di-t-butyl-2'-hydroxyphenyl)-5-chlorobenzotriazole, 2-(3'-t-butyl-2'-hydroxy-5'-methylphenyl)-5-chlorobenzotriazole, 2(2'-hydroxy-3',5'-di-t-butylphenyl)benzotriazole, 2(2'-hydroxy-3',5'-di-t-amylphenyl)benzotriazole, and 2-(2'-hydroxy-5-t-octylphenyl)benzotriazole. Addition of such UV stabilizers to polymeric films not only reduces UV light-induced degradation of those films in the long term, but also reduces film transmittance of UV light. Polymeric films formulated using such ultraviolet stabilizers are well known in the art, as are laminates of such UV stabilized film with, for example, metallized biaxially oriented polymeric film.

Transmittance properties of film laminates can also be controlled to some extent by the nature and components of the laminating adhesive used to adhere the component films forming the film laminate. Thus, UV absorbance of a film segment in accordance with this invention can be minimized by forming the segment from a film laminate using polymeric films (1) which inherently have UV absorbing functional groups, (2) which have been UV stabilized by the use of art-recognized UV stabilizers and (3) which have been laminated using adhesives comprising compounds having UV absorbing functional groups.

In a preferred embodiment the film segment has a transmittance value of less than about 0.001 for radiation having a wavelength from about 200 to about 320 nanometers and a transmittance value of less than about 0.01 for radiation having a wavelength ranging from about 320 to about 360 nanometers while at the same time being transparent to at least a portion of incident visible radiation. In a most preferred embodiment of the present invention the CW-shaped film segment is formed from a partially transparent film laminate comprising a biaxially oriented metallized polyethyleneterephthalate film and a medium to low density UV stabilized polyethylene or polyester film. Preferably the thickness of the film laminate is between about 2 mils and about 8 mils.

With reference to FIG. 6, the present eye protector can be formed to provide sufficient distance 30 between the eye and the eye proximal side of eye protector 2 when the protector is positioned in an adhesively retained position over the eye. The present invention thus provides the user of the eye protector ample space for comfortable eyelid and eyelash movement. This is particularly important in applications of the eye protector where the user needs to have at least some ability to "see" while the eye protector is in place.

Once the user discontinues the activity requiring eye protection or otherwise determines that eye protection is no longer required, the protective eyewear in accordance with the present invention can be easily removed from its location over the eyes by carefully peeling them from their adhesively retained positions. While the present eye protectors are designed to be disposable after use, their reuse is possible, but limited by the decreased effectiveness of the contact adhesive after first-time use.

The protective eyewear disclosed in the '002 and '962 patents are formed from ovoid or circular film segments having a scission line extending from the peripheral edge toward the geometric center of the film segment. It has been found that that construction can result in inadvertent tearing of the film segment during removal of the segment from the release paper backing or during manipulation of the film segment to form the eye protector. The endpoint of the scission line seems to provide a point where a tear is easily initiated. The present invention provides an advantage over the protective eyewear disclosed in the '002 and '962 patents in that the CW-shaped film does not tend to tear as readily during removal of the film segment from the release paper backing or during formation of the eye protector.

The present invention has been described in conjunction with the preferred embodiments. Those skilled in the art will appreciate that many modifications and changes may be made to the preferred embodiments without departing from the present invention as defined by the following claims.

We claim:

1. An improved eye protector for reducing exposure of an eye to ultraviolet radiation and potential eye irritants, said eye protector comprising an ultraviolet light absorbing polymer film segment transparent to at least a portion of incident visible light, said film segment having an eye proximal first side, an eye distal second side, and a peripheral edge, said peripheral edge defined at least in part by an opposing C-shaped portion and a W-shaped portion of the film segment, and a contact adhesive applied to a locus on the first side of the film segment, said locus of applied adhesive being coincident with at least a portion of the peripheral edge defined by the W-shaped portion of the film segment.

2. The eye protector of claim 1 wherein the radiation transmittance of the eye protector is less than about 0.001 for radiation having wavelength ranging from about 200 to about 320 nanometers and a value less than about 0.01 for radiation having a wavelength ranging from about 320 nanometers to about 360 nanometers.

3. The eye protector of claim 1 wherein the film segment comprises a biaxially oriented metallized polymeric film.

4. The eye protector of claim 3 wherein the biaxially oriented metallized polymeric film contains a UV absorbing compound.

5. The eye protector of claim 4 wherein the UV absorbing compound is selected from the group consisting of substituted benzophenone and substituted benzotriazole compounds.

6. The eye protector of claim 1 wherein the film segment is a layered film laminate wherein at least one polymeric film layer is a biaxially oriented metallized polymeric film.

7. The eye protector of claim 6 wherein the layered film laminate further comprises a UV absorbing polymeric film having a visible light transmittance of greater than 0.9.

8. The eye protector of claim 7 wherein the UV absorbing polymeric film layer of the composite layered film laminate is a low to medium density polyolefin or a polyester.

9. The eye protector of claim 8 wherein the UV absorbing polymeric film is selected from the group consisting of low to medium density polyethylene, polypropylene, and polyethyleneterephthalate.

10. The eye protector of claim 9 wherein the biaxially oriented metallized polymeric film layer is polyethyleneterephthalate.

11. The eye protector of claim 6 wherein the layers of the film laminate are laminated utilizing an adhesive in combination with a UV absorbing compound.

12. The eye protector of claim 11 wherein the biaxially oriented metallized film is metallized polyethyleneterephthalate.

13. An improved eye protector for reducing exposure of an eye to ultraviolet radiation and potential eye irritants, said eye protector comprising an ultraviolet light absorbing polymer film segment transparent to at least a portion of incident visible light, said film segment having an eye proximal first side, an eye distal second side, and a peripheral edge comprising C-shaped and W-shaped sections cooperating to define the peripheral edge, and a contact adhesive applied to a locus on the first side of the film segment, said locus of applied adhesive being coincident with at least a portion of the peripheral edge of the W-shaped section.

14. The eye protector of claim 13 wherein the radiation transmittance of the eye protector is less than about 0.001 for radiation having wavelength ranging from about 200 to about 320 nanometers and a value less than about 0.01 for radiation having a wavelength ranging from about 320 nanometers to about 360 nanometers.

15. The eye protector of claim 13 wherein the film segment comprises a biaxially oriented metallized polymeric film.

16. The eye protector of claim 15 wherein the biaxially oriented metallized polymeric film contains a UV absorbing compound.

17. The eye protector of claim 16 wherein the UV absorbing compound is selected from the group consisting of substituted benzophenone and substituted benzotriazole compounds.

18. The eye protector of claim 13 wherein the film segment is a layered film laminate wherein at least one polymeric film layer is a biaxially oriented metallized polymeric film.

19. The eye protector of claim 18 wherein the layered film laminate further comprises a UV absorbing polymeric film having a visible light transmittance of greater than 0.9.

20. The eye protector of claim 19 wherein the UV absorbing polymeric film layer of the composite layered film laminate is a low to medium density polyolefin or a polyester.

21. The eye protector of claim 20 wherein the UV absorbing polymeric film is selected from the group consisting of low to medium density polyethylene, polypropylene, and polyethyleneterephthalate.

22. The eye protector of claim 21 wherein the biaxially oriented metallized polymeric film layer is polyethyleneterephthalate.

23. The eye protector of claim 18 wherein the layers of the film laminate are laminated utilizing an adhesive in combination with a UV absorbing compound.

24. The eye protector of claim 23 wherein the biaxially oriented metallized film is metallized polyethyleneterephthalate.

25. A method for reducing the exposure of an eye to eye irritants and ultraviolet radiation, which method comprises forming a film segment having an eye proximal first side, an eye distal second side, and a peripheral edge, said peripheral edge defined at least in part by an opposing C-shaped portion and a W-shaped portion of the film segment, said W-shaped portion having first and second lobes, said film segment comprising a polymeric film having a radiation transmittance value of less than 1 for at least a portion of said ultraviolet radiation, and having a contact adhesive on a locus on one side of the shaped film segment, said locus being coincident with at least a portion of a peripheral edge of the shaped film segment, forming said segment into an asymmetric conical eye protector by overlapping and adhesively binding at least a portion of the first and second lobes of said W-shaped portion so that the peripheral edge of the segment essentially forms the base of the eye protector, and positioning said eye protector to cover the eye so that the base of the eye protector is in adhesive contact with the fleshy structures immediately adjacent the eye in the eye cavity, in which method the applied adhesive functions both as a shape retaining means for the eye protector and as a position retaining means when the eye protector is positioned to cover the eye.

26. The method of claim 25 wherein the film segment has an applied adhesive coincident with at least a portion of the W-shaped portion of the film segment and extending from a point on its peripheral edge toward the center of the segment, and the segment is formed into the asymmetric conical eye protector by overlapping the edges of the W-shaped portion of the film segment to adhesively engage said overlapped edges.

27. The method of claim 26 wherein the film segment is a layered polymeric film laminate.

28. The method of claim 27 wherein at least one layer of the polymeric film laminate is a biaxially oriented metallized polymeric film.

29. The method of claim 28 wherein the polymeric film laminate further comprises a UV absorbing polymeric film.

30. The method of claim 29 wherein the eye protector has a radiation transmittance value of less than 0.001 for radiation having a wavelength ranging from about 200 to about 320 nanometers and a value less than about 0.01 of radiation having a wavelength ranging from about 320 nanometers through about 360 nanometers and wherein the eye protector is transparent to at least a portion of incident visible radiation.

31. The method of claim 25 wherein the eye protector is formed from the shaped film segment by manipulating said segment to bring adjacent surfaces in the adhesive locus near the peripheral edge of the segment in adhesive contact forming an asymmetric cone.

* * * * *